United States Patent [19]

Fulker

[11] 4,102,346
[45] Jul. 25, 1978

[54] HEART PACEMAKER MONITOR, ALARM AND AUXILIARY POWER SUPPLY

[75] Inventor: Mabel H. Fulker, Tempe, Ariz.

[73] Assignee: The Raymond Lee Organization, Inc., New York, N.Y.; a part interest

[21] Appl. No.: 829,612

[22] Filed: Sep. 1, 1977

[51] Int. Cl.² .............................................. A61N 1/36
[52] U.S. Cl. ......................... 128/419 PS; 128/419 PT
[58] Field of Search ................... 128/419 PG, 419 PS, 128/419 PT

[56] References Cited

U.S. PATENT DOCUMENTS

| | | | |
|---|---|---|---|
| 3,517,663 | 6/1970 | Bowers et al. | 128/419 PT |
| 3,618,615 | 11/1971 | Greatbatch | 128/419 PG |
| 3,748,500 | 7/1973 | Tam | 128/419 PS |
| 3,841,336 | 10/1974 | Daynard | 128/419 PT |
| 3,866,614 | 2/1975 | Svensson | 128/419 PG |
| 4,026,305 | 5/1977 | Brownlee et al. | 128/419 PS |

*Primary Examiner*—William E. Kamm
*Attorney, Agent, or Firm*—Daniel Jay Tick

[57] ABSTRACT

A monitor device electronically connected to a pacemaker and to an alarm device counts the pulses supplied to the heart by the pacemaker, detects the signal level of the pulses and compares the number of pulses with a preselected number and the signal level with a preselected signal level. The monitor device connects an auxiliary battery source of power to the pacemaker and actuates the alarm device when the detected number is less than the preselected number and when the detected level is less than the preselected level.

3 Claims, 1 Drawing Figure

U.S. Patent    July 25, 1978    4,102,346
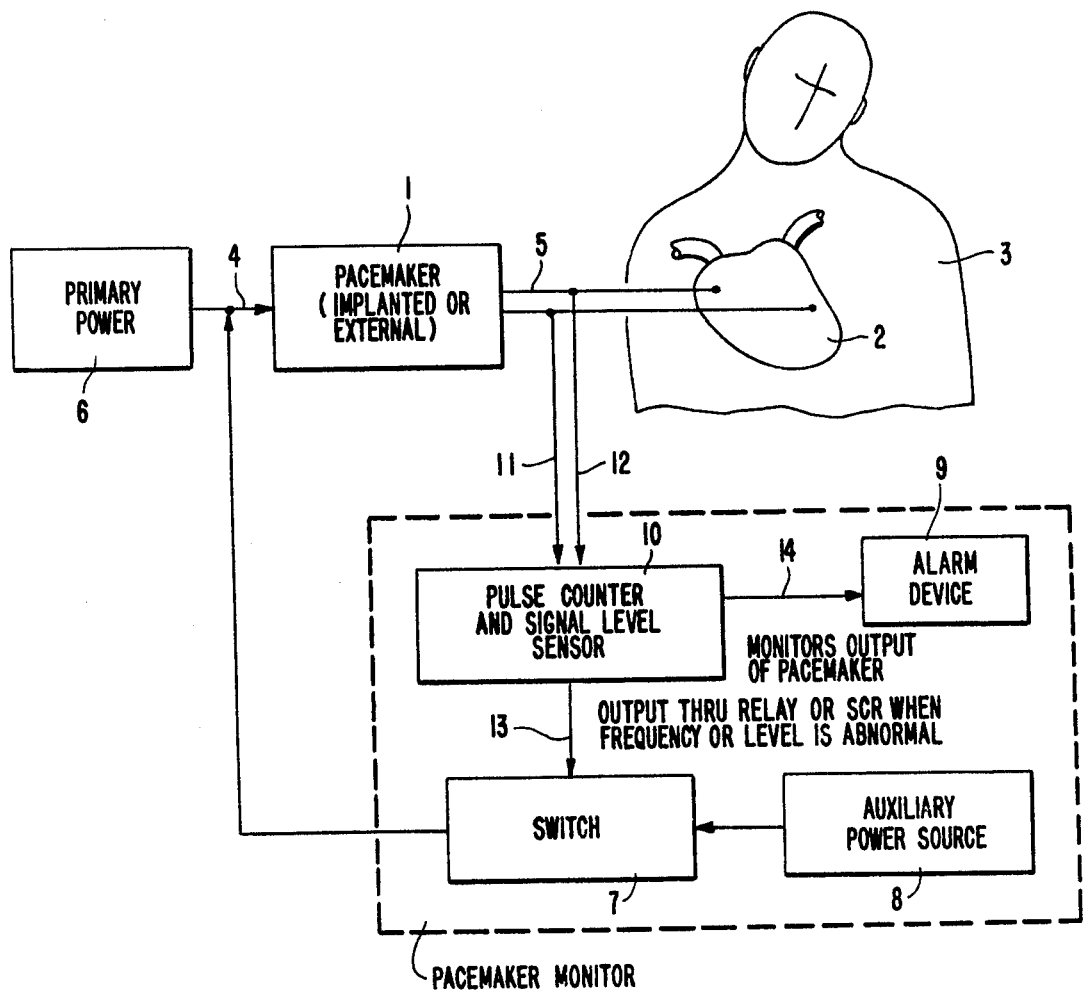

HEART PACEMAKER MONITOR, ALARM AND AUXILIARY POWER SUPPLY

BACKGROUND OF THE INVENTION

The present invention relates to a pacemaker monitor. More particularly, the invention relates to a pacemaker monitor for a pacemaker of a human heart, said pacemaker having an input, a primary battery source of power electrically connected to its input, and an output electrically connected to the heart of a user.

Objects of the invention are to provide a pacemaker monitor of simple structure, which is inexpensive in manufacture, installed with facility and convenience by electrical connection internally or externally to the pacemaker of a human heart, and functions efficiently, effectively and reliably to warn the user of the pacemaker when it is malfunctioning and when the primary battery source of power of the pacemaker is dissipated or malfunctioning thereby serving to save the life of such user.

BRIEF DESCRIPTION OF THE DRAWINGS

In order that the invention may be readily carried into effect, it will now be described with reference to the accompanying drawing, wherein the single FIGURE is a block diagram of an embodiment of the pacemaker monitor of the invention.

DETAILED DESCRIPTION OF THE INVENTION

The pacemaker monitor of the invention is for a pacemaker 1 of a human heart 2. The pacemaker 1 is of any suitable type and is coupled to a user 3 either externally or by implantation in the body of the user, in the usual manner. The pacemaker 1 has an input 4 and an output 5 electrically connected to the heart 2 of the user 3, as shown in the FIGURE.

A primary battery source of power 6 of the usual known type is electrically connected to the input 4 of the pacemaker 1.

The pacemaker monitor of the invention comprises a switch 7 electrically connecting an auxiliary power source 8 to the input 4 of the pacemaker 1. The auxiliary power source 8 comprises an auxiliary battery of the same type as the primary battery source of power 6.

The pacemaker monitor further comprises an alarm device 9 of any suitable type, which is preferably an audible alarm, which, when actuated, makes sufficient noise to attract the attention of the user 3.

In accordance with the invention, the pacemaker monitor also includes a monitor device 10 having inputs 11 and 12 electrically connected to the output 5 of the pacemaker 1. The monitor device 10 has an output 13 electrically connected to the switch 7 and an output 14 electrically connected to the alarm device 9. The monitor device 10 includes a pulse counter of any suitable type for counting the pulses supplied to the heart 2 by the pacemaker 1. The monitor device 10 also includes a signal level detector of any suitable type for detecting the signal level of the pulses supplied to the heart by the pacemaker.

The monitor device 10 further includes a comparator of any suitable type for comparing the number of pulses supplied to the heart with a preselected number, and also comparing the signal level with a preselected signal level. The comparator of the monitor device 10 closes the switch 7 to connect the auxiliary battery source of power to the pacemaker 1 and actuates the alarm device 9 when the detected number is less than the preselected number and when the detected level is less than the preselected level.

The auxiliary battery source of power thus takes over the function of the failing pacemaker to maintain the transfer of electrical signals to said pacemaker when primary battery source of power is weakened. The auxiliary battery source of power is actually connected to a miniature pacemaker so that the auxiliary battery and the miniature pacemaker and the auxiliary battery keep the patient alive.

Since the combination of the auxiliary battery source of power and the miniature pacemaker of the invention are external to the body of the user 3, it is unnecessary to surgically operate to replace the pacemaker batteries, etc. This is very important, especially to elderly and very ill people.

While the invention has been described by means of a specific example and in a specific embodiment, I do not wish to be limited thereto, for obvious modifications will occur to those skilled in the art without departing from the spirit and scope of the invention.

I claim:

1. A pacemaker monitor for a pacemaker of a human heart, such pacemaker having an input, a primary battery source of power electrically connected to its input, and an output electrically connected to the heart of a user, said pacemaker monitor comprising an auxiliary battery source of power;

switch means electrically connecting the auxiliary battery source of power to the input of the pacemaker;

an alarm device; and a monitor device having inputs electrically connected to the output of the pacemaker and outputs electrically connected to the switch means and to the alarm device for counting the pulses supplied to the heart by the pacemaker, detecting the signal level of such pulses and comparing the number of pulses with a preselected number and the signal level with a preselected signal level and closing the switch means to connect the auxiliary battery source of power to the pacemaker and actuating the alarm device when the detected number is less than the preselected number and when the detected level is less than the preselected level.

2. A pacemaker monitor as claimed in claim 1, wherein the auxiliary battery source of power is external to the body of the user.

3. A pacemaker monitor as claimed in claim 2, wherein the pacemaker is external to the body of the user.

* * * * *